(12) United States Patent
Nitta

(10) Patent No.: US 10,036,377 B2
(45) Date of Patent: Jul. 31, 2018

(54) PUMP UNIT AND RESPIRATORY ASSISTANCE DEVICE

(71) Applicant: Metran Co., Ltd., Kawaguchi-shi, Saitama (JP)

(72) Inventor: Kazufuku Nitta, Saitama (JP)

(73) Assignee: METRAN CO., LTD., Kawaguchi-shi, Saitama (JP)

( * ) Notice: Subject to any disclaimer, the term of this patent is extended or adjusted under 35 U.S.C. 154(b) by 936 days.

(21) Appl. No.: 14/362,808

(22) PCT Filed: Dec. 5, 2012

(86) PCT No.: PCT/JP2012/081467
§ 371 (c)(1),
(2) Date: Jun. 4, 2014

(87) PCT Pub. No.: WO2013/084918
PCT Pub. Date: Jun. 13, 2013

(65) Prior Publication Data
US 2014/0305436 A1    Oct. 16, 2014

(30) Foreign Application Priority Data
Dec. 8, 2011   (JP) ................. 2011-268659

(51) Int. Cl.
*F04B 43/04*   (2006.01)
*A61M 15/00*   (2006.01)
(Continued)

(52) U.S. Cl.
CPC ....... *F04B 43/043* (2013.01); *A61M 15/0085* (2013.01); *A61M 15/025* (2014.02);
(Continued)

(58) Field of Classification Search
CPC ..... A61M 16/0012; A61M 16/127; F04F 5/16
See application file for complete search history.

(56) References Cited

U.S. PATENT DOCUMENTS

| | | | | |
|---|---|---|---|---|
| 3,581,742 A | * | 6/1971 | Glenn .................. | A61M 16/00 128/204.19 |
| 3,859,995 A | * | 1/1975 | Colston .................. | B63C 11/24 128/204.25 |

(Continued)

FOREIGN PATENT DOCUMENTS

| | | |
|---|---|---|
| DE | 309595 C | 5/1916 |
| EP | 1 830 085 A1 | 9/2007 |

(Continued)

OTHER PUBLICATIONS

Supplementary Partial European Search Report for EP 2 781 748, dated Nov. 25, 2014.

(Continued)

*Primary Examiner* — Kenneth J Hansen
(74) *Attorney, Agent, or Firm* — Flynn, Thiel, Boutell & Tanis, P.C.

(57) ABSTRACT

A pump unit includes a micro pump and an assist mechanism. The micro pump includes: a housing having an inflow port and an outflow port; and a pump device built in the housing, the pump device transporting a fluid from the inflow port to the outflow port. The assist mechanism includes a jet nozzle for jetting a fluid. A jet port is opened at a tip portion of the jet nozzle. The assist mechanism is disposed in such a manner that a gap through which a fluid outside can flow is formed between the tip portion and the housing. The jet port is located in proximity to the inflow port. The jet port directly faces the inflow port.

9 Claims, 20 Drawing Sheets

(51) Int. Cl.
*F04B 19/00* (2006.01)
*A61M 15/02* (2006.01)
*A61M 16/00* (2006.01)
*F04F 5/16* (2006.01)
*A61M 16/12* (2006.01)
*A61M 16/06* (2006.01)

(52) U.S. Cl.
CPC .... *A61M 16/0012* (2014.02); *A61M 16/0057* (2013.01); *A61M 16/0096* (2013.01); *A61M 16/127* (2014.02); *F04B 19/006* (2013.01); *F04F 5/16* (2013.01); *A61M 16/06* (2013.01); *A61M 2016/0027* (2013.01); *A61M 2016/0039* (2013.01); *A61M 2202/0208* (2013.01); *A61M 2205/8206* (2013.01); *A61M 2210/0618* (2013.01)

(56) References Cited

U.S. PATENT DOCUMENTS

| | | |
|---|---|---|
| 6,179,586 B1 | 1/2001 | Herb et al. |
| 8,678,787 B2 | 3/2014 | Hirata et al. |
| 2005/0008545 A1 | 1/2005 | Bessho et al. |
| 2005/0074340 A1 | 4/2005 | Xu et al. |
| 2009/0232682 A1 | 9/2009 | Hirata et al. |
| 2009/0232683 A1 | 9/2009 | Hirata et al. |

FOREIGN PATENT DOCUMENTS

| | | |
|---|---|---|
| EP | 1 905 590 A2 | 4/2008 |
| EP | 1 905 590 A3 | 3/2013 |
| FR | 2 597 754 A1 | 10/1987 |
| GB | 1 237 273 A | 6/1971 |
| GB | 2 117 648 A | 10/1983 |
| JP | 49-97308 A | 9/1974 |
| JP | 62-261370 A | 11/1987 |
| JP | 4-43875 A | 2/1992 |
| JP | 10-510182 A | 10/1998 |
| JP | 2010-281331 A | 12/2010 |
| JP | 934751 B1 | 2/2012 |
| JP | 4934751 131 | 5/2012 |
| WO | WO 96/17641 A1 | 6/1996 |
| WO | WO 97/024528 A2 | 7/1997 |
| WO | WO 01/037911 A1 | 5/2001 |
| WO | WO 2008/069266 A1 | 6/2008 |

OTHER PUBLICATIONS

Supplementary European Search Report for EP 2 781 748, dated Apr. 30, 2015.
International Search Report issued in PCT/JP2012/081467 with English translation dated Mar. 12, 2013 (5 pages).

* cited by examiner

PUMP UNIT AND RESPIRATORY ASSISTANCE DEVICE

TECHNICAL FIELD

The present invention relates to a pump unit that transports a fluid by means of a micro pump and a respiratory assistance device employing the same.

BACKGROUND ART

In medical practice, respiratory assistance devices, such as artificial respirators are in use. The respiratory assistance devices employ methods such as a controlled ventilation (Controlled Ventilation) method used for a patient in the absence of spontaneous breathing (a patient under general anesthesia, during cardiopulmonary resuscitation, or in a critical condition), an assisted ventilation (Assisted Ventilation) method for creating a positive pressure in a respiratory tract in accordance with the spontaneous breathing of a patient, a partial assisted ventilation (Assist/Control) method using the assisted ventilation and the controlled ventilation in combination, and a high frequency oscillation ventilation method for realizing a very small amount of a single ventilation of 1 to 2 ml/kg by causing a gas supplied by an respiratory tract to oscillate at a frequency of 5 to 40 Hz.

The respiratory assistance device is used also for a patient with a respiratory disorder during sleep. This respiratory disorder is caused by the blockage of a respiratory tract as a result of relaxation of the muscle of the respiratory tract during sleep and the resultant retraction of the posterior part of a tongue or a soft palate. Creating a positive pressure in a respiratory tract alleviates the symptom of a patient with this type of respiratory disorder.

Any of the respiratory assistance devices requires a pump unit for creating a positive pressure in a respiratory tract. A blower that transports a gas by the rotation of a fan, a cylinder pump that transports a gas by the reciprocal motion of a piston, or the like is used as a power source for this pump unit.

SUMMARY OF INVENTION

Technical Problem

However, this pump unit is relatively large in the conventional respiratory assistance device. Thus, the pump unit is housed in a box-shaped housing and is placed beside a user when used. Therefore, there is a problem in that downsizing of the respiratory assistance device is difficult to achieve.

As shown in FIG. 20, for example, during an inspiratory operation (X in the figure), the pump unit used in the respiratory assistance device initially increases a pressure (creates a positive pressure) rapidly at a high flow rate and thereafter maintains a constant flow rate while assisting inspiration by further increasing a respiratory tract internal pressure P. During an expiratory operation (Y in the figure), the pump unit decreases a pressure (creates a negative pressure) rapidly at a high flow rate Q and gradually decreases the flow rate Q if the respiratory tract internal pressure P starts to decrease in order to make control so as not to place a burden on a lung. Such control is merely one example and various control modes are required in reality. However, fine control of this type requires the employment of a relatively large blower or cylinder pump in order to freely change the respiratory tract internal pressure P and the flow rate Q. Therefore, this makes it more difficult to downsize the pump unit.

The present invention has been made in view of the aforementioned problems and it is an object of the present invention to provide a pump unit capable of freely controlling the respiratory tract internal pressure P and the flow rate Q and also achieving significant downsizing, and a respiratory assistance device employing the same.

Solution to Problem

A pump unit that achieves the aforementioned object is configured by a plurality of pump bodies each of which introduces a fluid outside a housing into the housing through an inlet formed in a surface of the housing and discharges the introduced fluid to the outside of the housing through an outlet formed in the housing by means of a pump device housed in the housing. The pump unit includes a jet nozzle provided at the outlet of the pump body on an upstream side, the jet nozzle including a jet port in a tip portion thereof and disposed at a position where a gap is formed by a peripheral portion of the inlet of the pump body on a downstream side and the tip portion.

Preferably, the jet port directly faces the inlet.

The pump unit preferably includes a tubular flow passage forming member projecting from the surface of the housing at the peripheral portion of the inlet of the pump body on the downstream side, the tubular flow passage forming member forming a flow passage of a fluid jetted from the jet port. Moreover, the flow passage forming member preferably has a narrowing part expanding in a direction from the housing toward the jet nozzle. Furthermore, the flow passage forming member preferably has an expanding part expanding in a direction from the jet nozzle toward the housing. In addition, the jet port is preferably positioned inside the flow passage forming member.

The tip portion is preferably passed through the inlet.

The jet nozzle preferably expands toward the tip portion.

The pump device preferably includes an inflow port for allowing the fluid to flow in and an outflow port for allowing the fluid to flow out. The housing of the pump body on the upstream side preferably houses a first inlet side pump device having the inflow port directly connected to a first inlet of the inlets, a second inlet side pump device having the inflow port directly connected to a second inlet of the inlets, an outlet side pump device having the outflow port directly connected to the outlet, and a confluent passage forming member that merges the fluids exiting from the outflow ports of the first and second inlet side pump devices and sends the merged fluid to the inflow port of the outlet side pump device.

A respiratory assistance device that achieves the aforementioned object includes: a flow passage through which an expiratory or inspiratory gas passes; a nozzle disposed in the flow passage, the nozzle jetting an acceleration gas in an expiratory or inspiratory direction; and the pump unit fixed around the flow passage, the pump unit supplying the acceleration gas to the nozzle.

The respiratory assistance device preferably includes a Venturi wall provided in the flow passage, the Venturi wall spreading out the acceleration gas jetted from the nozzle. The nozzle preferably includes: an inspiratory nozzle disposed in the flow passage, the inspiratory nozzle jetting an acceleration gas in an inspiratory direction; and an expiratory nozzle disposed closer to an expiratory direction side than the inspiratory nozzle in the flow passage, the expiratory nozzle jetting an acceleration gas in the expiratory direction. The Venturi wall preferably includes: an inspiratory Venturi wall provided in the flow passage so as to extend from the inspiratory nozzle in the inspiratory direction, the inspiratory Venturi wall causing the acceleration gas released from the inspiratory nozzle to be spread out to create a larger negative pressure in the inspiratory direction side than in the inspiratory nozzle; and an expiratory Venturi wall provided in the flow passage so as to extend from the expiratory nozzle in the expiratory direction, the expiratory Venturi wall causing the acceleration gas released from the expiratory nozzle to be spread out to create a larger negative pressure in the expiratory direction side than in the expiratory nozzle.

A respiratory assistance device that achieves the aforementioned object includes: a flow passage through which an expiratory or inspiratory gas passes; an inspiratory nozzle disposed in the flow passage, the inspiratory nozzle jetting an acceleration gas in an inspiratory direction; an expiratory nozzle disposed closer to an expiratory direction side than the inspiratory nozzle in the flow passage, the expiratory nozzle jetting an acceleration gas in the expiratory direction; a pump unit for supplying the acceleration gas to the inspiratory nozzle and the expiratory nozzle; an inspiratory Venturi wall provided in the flow passage so as to extend from the inspiratory nozzle in the inspiratory direction, the inspiratory Venturi wall causing the acceleration gas released from the inspiratory nozzle to be spread out to create a larger negative pressure in the inspiratory direction side than in the inspiratory nozzle; and an expiratory Venturi wall provided in the flow passage so as to extend from the expiratory nozzle in the expiratory direction, the expiratory Venturi wall causing the acceleration gas released from the expiratory nozzle to be spread out to create a larger negative pressure in the expiratory direction side than in the expiratory nozzle.

Preferably, the inspiratory Venturi walls are provided in the flow passage so as to interpose a jet port of the inspiratory nozzle therebetween, and the expiratory Venturi walls are provided in the flow passage so as to interpose a jet port of the expiratory nozzle therebetween.

Advantageous Effects of Invention

According to the present invention, an excellent effect such that the pump unit can be significantly downsized while maintaining an ability to freely control a pressure and a flow rate can be provided.

DESCRIPTION OF EMBODIMENTS

Exemplary embodiments of the present invention will now be described below in detail with reference to the drawings.

Figure 1:
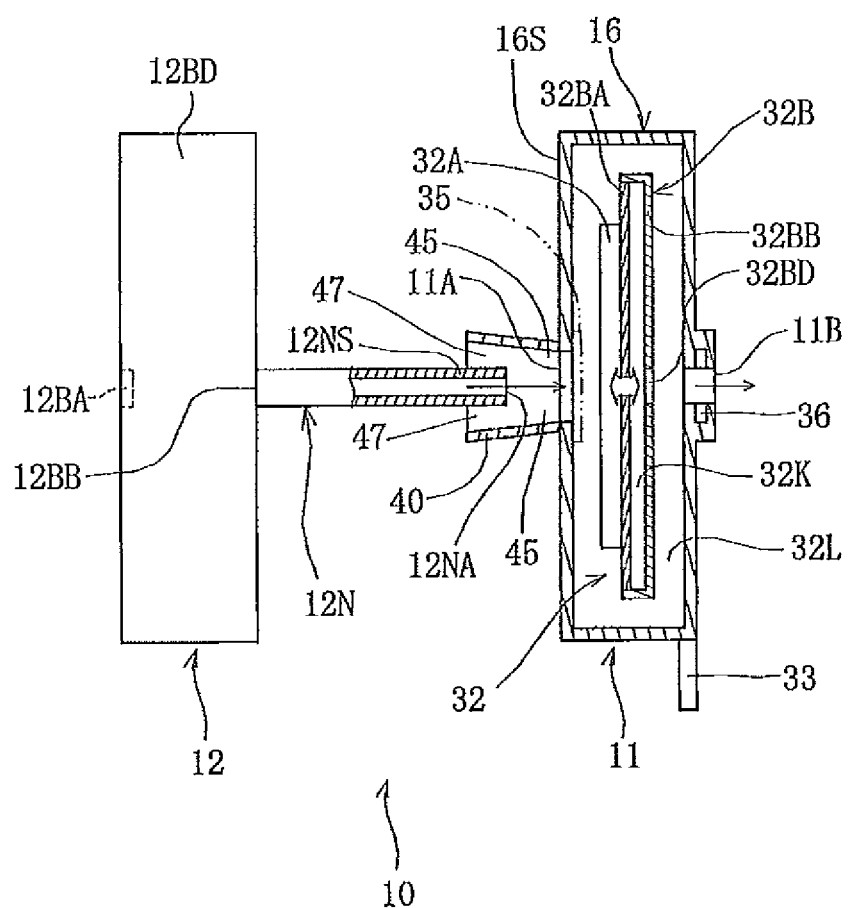
FIG. 1 is a partial cross-sectional view illustrating an outline of a first pump unit including a first assist mechanism and a first micro pump.

As shown in FIG. 1, a pump unit 10 includes a micro pump 11 and an assist mechanism 12.

Figure 2:
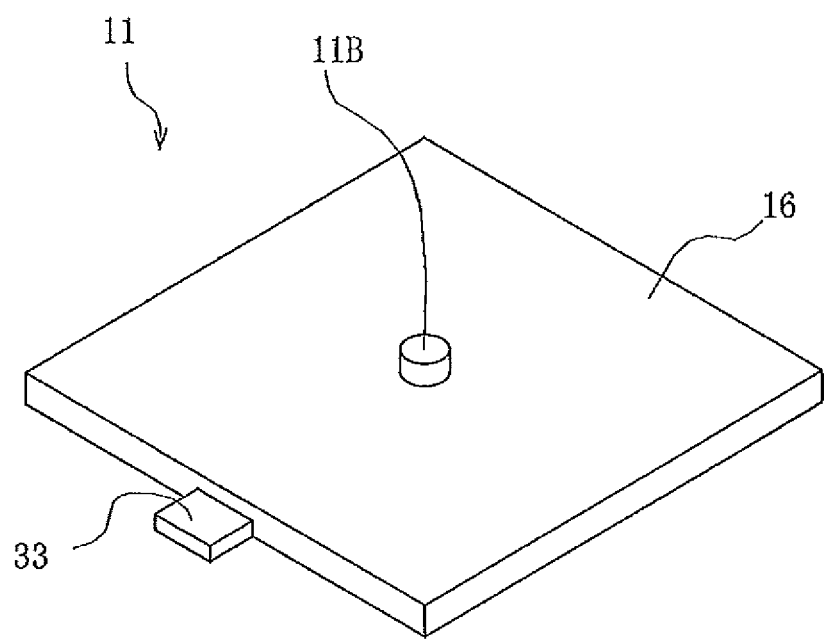
FIG. 2 is a perspective view illustrating the outline of the micro pump.

A micro pump proposed in Patent Literature WO 2008/069266, for example, can be used as the micro pump 11. As shown in FIGS. 1 and 2, the micro pump 11 includes: a housing 16 having an inflow port 11A and an outflow port 11B formed therein; a pump device 32 built in the housing 16, the pump device transporting a fluid from the inflow port 11A to the outflow port 11B; and a power-supplying terminal 33 exposed to the outside of the housing 16. The actuation of the pump device 32 causes a fluid to be sucked from the inflow port 11A and causes the fluid to be jetted from the outflow port 11B.

The pump device 32 is electrically connected to the power-supplying terminal 33. The pump device 32 includes: a piezoelectric element 32A deformable with the application of a voltage; and a deformable box 32B deformable by the actuation of the piezoelectric element. The deformable box 32B includes a diaphragm 32BA and an oscillation wall 32BB. The diaphragm 32BA is provided in a portion of the deformable box 32B facing the inflow port 11A. The oscillation wall 32BB is provided in a portion of the deformable box 32B facing the outflow port 11B. A primary blower chamber 32K is formed inside the deformable box 32B, i.e., between the diaphragm 32BA and the oscillation wall 32BB. In the oscillation wall 32BB, an opening 32BD through which the fluid is moved between the inside and outside of the primary blower chamber 32K is formed at a position directly facing the outflow port 11B. The piezoelectric element 32A is attached to a surface of the diaphragm 32BA facing the inflow port 11A.

When the diaphragm 32BA is oscillated by the piezoelectric element 32A, the fluid is moved between a secondary blower chamber 32L formed by the housing 16 and the pump device 32 and the primary blower chamber 32K. The movement of the fluid causes the oscillation wall 32BB to resonate. The oscillation of the diaphragm 32BA and the oscillation wall 32BB causes a fluid to be sucked from the inflow port 11A. The fluid sucked from the inflow port 11A is passed through the secondary blower chamber 32L and released from the outflow port 11B. The micro pump 11 is suitable for use as a blower for transporting a fluid. The micro pump 11 can transport a fluid without employing a check valve.

The frequency of the diaphragm 32BA is greater than or equal to 1 kHz, for example, and preferably in an inaudible range (for example, 18 kHz or more and 27 kHz or less). If the frequency of the diaphragm 32BA is in the inaudible range, even when a device (for example, a respiratory assistance device) having the pump device 32 is worn at a predetermined part of a patient (especially a part closer to an ear), the patient cannot hear the operational noise of the pump device 32. Thus, it is prevented from giving discomfort caused by the operational noise to the patient.

The micro pump 11 further includes sensor units 35 and 36. The sensor unit 35 includes: a pressure sensor that detects a static pressure P of a fluid at the inflow port 11A; and a flow sensor that detects a flow rate Q of the fluid at the inflow port 11A. The sensor unit 36 includes: a pressure sensor that detects a static pressure P of a fluid at the outflow port 11B; and a flow sensor that detects a flow rate Q of the fluid at the outflow port 11B.

The micro pump 11 is formed in a plate shape and extremely small (about 20 mm in length×20 mm in width×2 mm in thickness, for example). Nevertheless, the micro pump 11 can transport a fluid of up to about 1 L/min when the input sine wave is set at 26 kHz under 15 Vpp (Volt peak to peak) and can obtain a static pressure of up to 2 kPa (see FIG. 3).

Furthermore, an inner diameter of the outflow port 11B in the micro pump 11 is relatively small, for example, smaller than or equal to 2 mm, preferably smaller than or equal to 1 mm.

Figure 3:
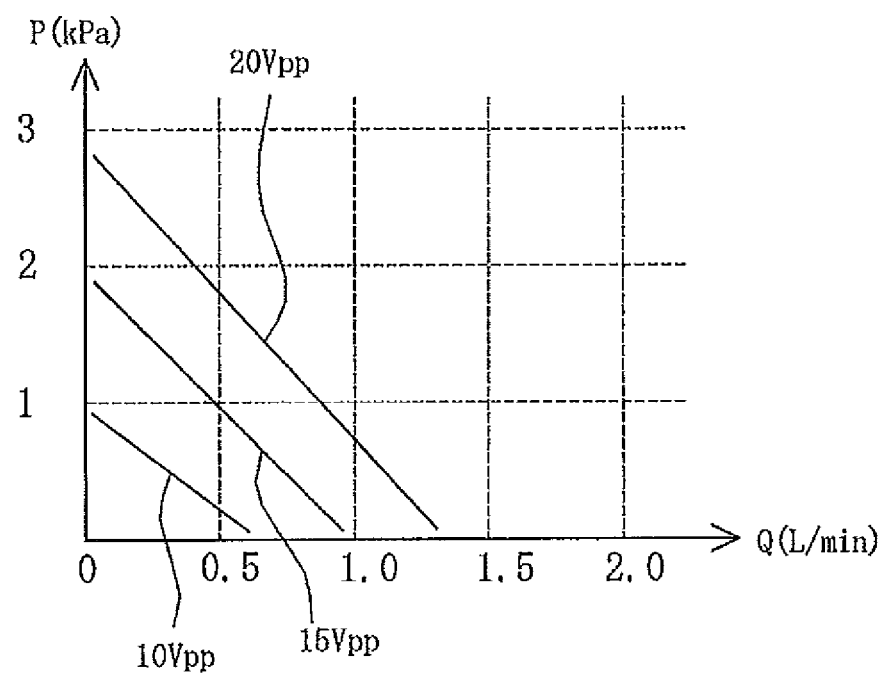
FIG. 3 is a graph showing pressure-flow rate lines for the micro pump.

Since the micro pump 11 transports a fluid by the oscillation of the diaphragm 32BA caused by the piezoelectric element 32A, there is naturally a limit in the volume of a fluid the micro pump 11 can transport. The static pressure-flow rate characteristics exhibit a trend as shown in FIG. 3 (for example, a linear function with a negative proportionality multiplier or something similar). For example, to obtain a static pressure of about 1 kPa, the flow rate Q is 0.5 L/min. When the input sine wave is changed to 10 Vpp or 20 Vpp, the amplitude of the piezoelectric element 32A is changed. Thus, the flow rate Q and the static pressure P according to the input sine wave can be obtained. Specifically, if the Vpp of the input sine wave is smoothly changed, the flow rate Q and the static pressure P can be smoothly changed. Alternatively, if the frequency of the input sine wave is changed, the flow rate Q and the static pressure P can be changed. Thus, if the frequency of the input sine wave is smoothly changed, the flow rate Q and the static pressure P can be smoothly changed. Note however that the flow rate Q and the static pressure P each have an upper limit depending on the performance of the piezoelectric element 32A and the strength or durability of components in the micro pump 11. The micro pump 11 is generally used at a rated Vpp and a rated frequency.

Note that the micro pump 11 may have a monomorph (unimorph) structure as described above in which a single piezoelectric element 32A is attached to the diaphragm 32BA or a bimorph structure in which two piezoelectric elements 32A are attached to each other in order to increase the amount of oscillation. An appropriate structure of the micro pump 11 may be selected depending on its purpose such as the transportation of a fluid. While the micro pump 11 can transport a fluid without employing a check valve, the micro pump 11 may be replaced by a micro pump including a check valve at the inflow port or the outflow port.

Referring back to FIG. 1, the assist mechanism 12 includes: a pump body 12BD having an intake port 12BA for taking a fluid in and a send-out port 12BB for sending out the fluid; and a cylindrical jet nozzle 12N attached to the send-out port 12BB, the jet nozzle 12N jetting the fluid taken into the pump body 12BD. A jet port 12NA is opened at a tip portion 12NS of the jet nozzle 12N.

The pump unit 10 further includes a cylindrical flow passage forming tube 40. The flow passage forming tube 40 is configured to form a flow passage of the fluid jetted from the jet port 12NA. The flow passage forming tube 40 is formed so as to project from a facing surface 16S of the housing 16 facing the assist mechanism 12 at a peripheral portion of the inflow port 11A.

The jet port 12NA is positioned inside the flow passage forming tube 40. The flow passage forming tube 40 is formed so as to expand from the micro pump 11 toward the assist mechanism 12. While the flow passage forming tube 40 shown in FIG. 1 is expanded at a constant rate, the flow passage forming tube 40 may alternatively have a shape whose degree of expansion is increased as it is away from the micro pump 11.

Figure 4:
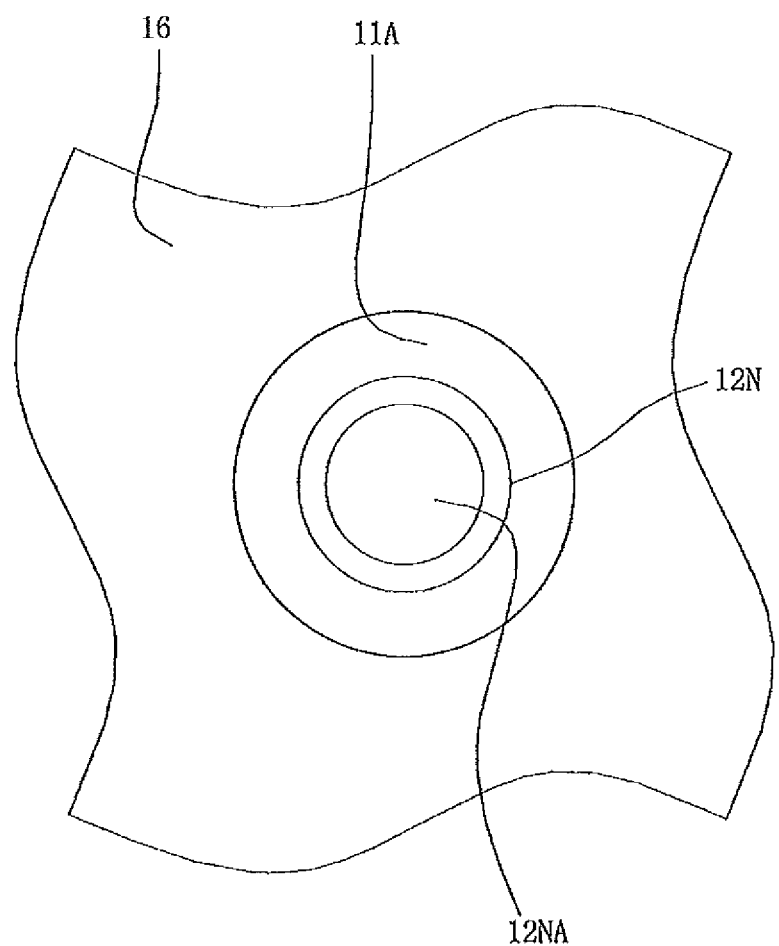
FIG. 4 is a side view of a jet nozzle as viewed from a secondary blower chamber side.

The assist mechanism 12 is disposed in such a manner that a gap 47 through which a fluid outside the micro pump 11 can flow is formed between the tip portion 12NS and the flow passage forming tube 40. It is preferable that the jet port 12NA be located in proximity to the inflow port 11A. It is also preferable that the jet port 12NA be located directly facing the inflow port 11A. The opening size of the jet port 12NA is smaller than that of the inflow port 11A. Specifically, the opening shape of the jet port 12NA is confined within the opening shape of the inflow port 11A (see FIG. 4). The opening shape of the inflow port 11A and the jet port 12NA may be any shape such as a circle, an ellipse, or a polygon.

The assist mechanism 12 may be composed of the micro pump 11 serving as the pump body 12BD and the jet nozzle 12N attached to the outlet 11B of the micro pump 11, for example.

Figure 5:
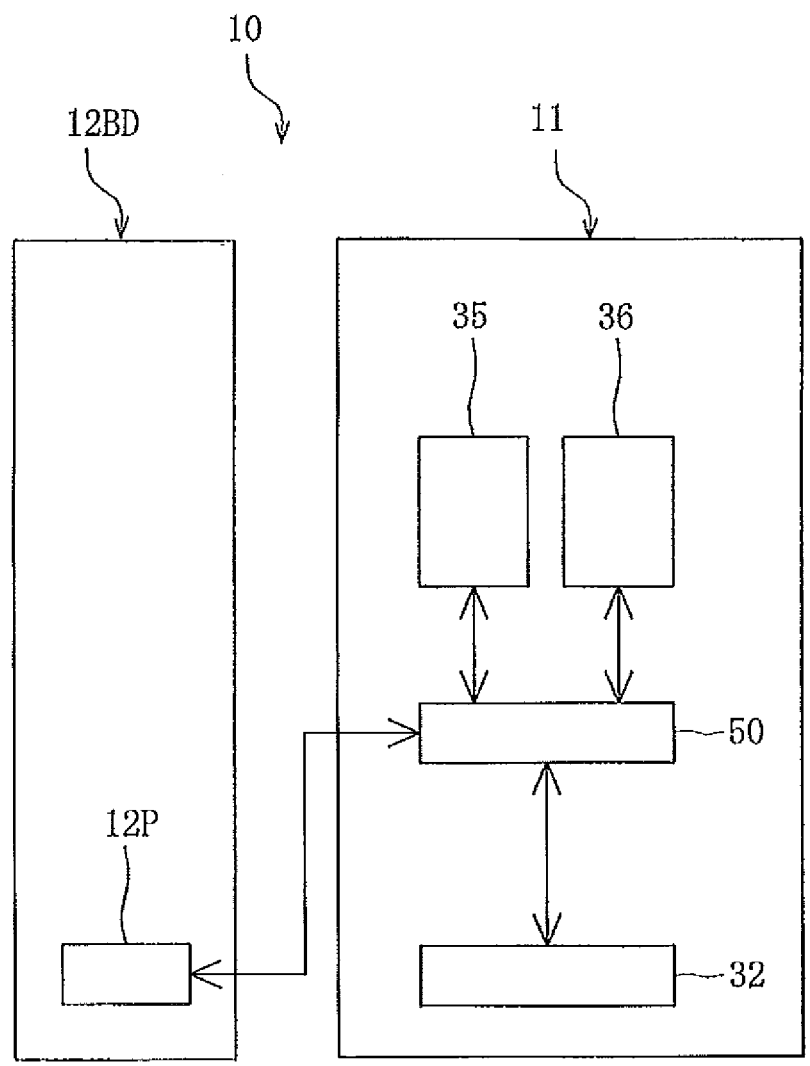
FIG. 5 is a block diagram illustrating an outline of a controller.

As shown in FIG. 5, the pump unit 10 includes a controller 50. The controller 50 electrically connects to a pump part 12P built in the pump body 12BD, the pump device 32, and the respective sensor units 35 and 36. The controller 50 reads sensing signals from the sensors in the respective sensor units 35 and 36. Furthermore, the controller 50 controls the pump device 32 and the pump part 12P so as to obtain a predetermined static pressure P and flow rate Q at the outlet 11B. The pump device 32 and the pump part 12P can be controlled by appropriately setting power supply conditions (a voltage value, a voltage frequency, and the like) in the pump device 32 and the pump part 12P. When the sensor units 35 and 36 are omitted, the controller 50 may perform control on the basis of data associating the power supply conditions in the pump device 32 and the pump part 12P with the static pressure P and the flow rate Q at the outlet 11B. This data is stored in an internal memory in the controller, for example.

When the micro pump 11 is used as the pump body 12BD, the pump device 32 corresponds to the pump part 12P.

Operation of the pump unit 10 will be described next. Under the control of the controller 50 (see FIG. 5), the pump part 12P and the pump device 32 are operated. As shown in FIG. 1, the operation of the pump device 32 causes a fluid in the vicinity of an opening end of the flow passage forming tube 40 to pass through the inflow port 11A and the secondary blower chamber 32L sequentially. The fluid introduced into the secondary blower chamber 32L is released from the outflow port 11B by the operation of the pump device 32.

The operation of the pump part 12P causes a fluid to be jetted from the jet port 12NA. Since the jet port 12NA is located in proximity to the inflow port 11A, the fluid jetted from the jet port 12NA directly passes through the inflow port 11A and flows into the secondary blower chamber 32L. A fluid present in a gap 45 formed by the jet nozzle 12N and the peripheral portion of the inflow port 11A flows toward the secondary blower chamber 32L by being pulled by the fluid jetted from the jet port 12NA and flowing toward the secondary blower chamber 32L. Furthermore, a fluid present in the gap 47 also flows toward the secondary blower chamber 32L by being pulled by the fluid flowing toward the secondary blower chamber 32L. Consequently, the gap 45 and the gap 47 can be set at a negative pressure. Therefore, as compared to a case where only the micro pump 11 is used for operation, the flow rate of a fluid at the inflow port 11A can be increased. Thus, according to the pump unit 10, the flow rate of a fluid at the outflow port 11B can be increased as compared to a case where only the micro pump 11 is used for operation. Furthermore, the flow rate of a fluid at the outflow port 11B can be set more finely by individually controlling the power supply conditions of the pump part 12P and the pump device 32 as compared to a case where only the micro pump 11 is used for operation.

As described above, since the inner diameter of the outflow port 11B in the micro pump 11 is small to some extent, the oscillation of the diaphragm 32BA can cause a fluid to continuously flow out from the outflow port 11B without providing a check valve. On the other hand, the smallness in the inner diameter of the outflow port 11B limits the volume of a fluid that can flow out from the outflow port 11B. Thus, in order to increase the volume of a fluid to flow out to some extent, a plurality of micro pumps can be connected in series, instead of employing a single micro pump 11, in such a manner that a second micro pump (corresponding to the assist mechanism 12 in FIG. 1) is arranged before the micro pump 11 (corresponding to the micro pump 11 in FIG. 1), a third micro pump is arranged before the second micro pump, and so forth. However, it is sometimes difficult to connect a plurality of (three or more, for example) micro pumps in series. According to the pump unit 10, increasing the volume of a fluid to flow out from the outflow port 11B to some extent can be easily achieved without connecting a plurality of micro pumps in series.

It is preferable that the gap 47 be annularly formed around the circumference of the tip portion 12NS. Note that the gap 47 may be formed in a circular arc shape or an elliptical arc shape.

Figure 6:
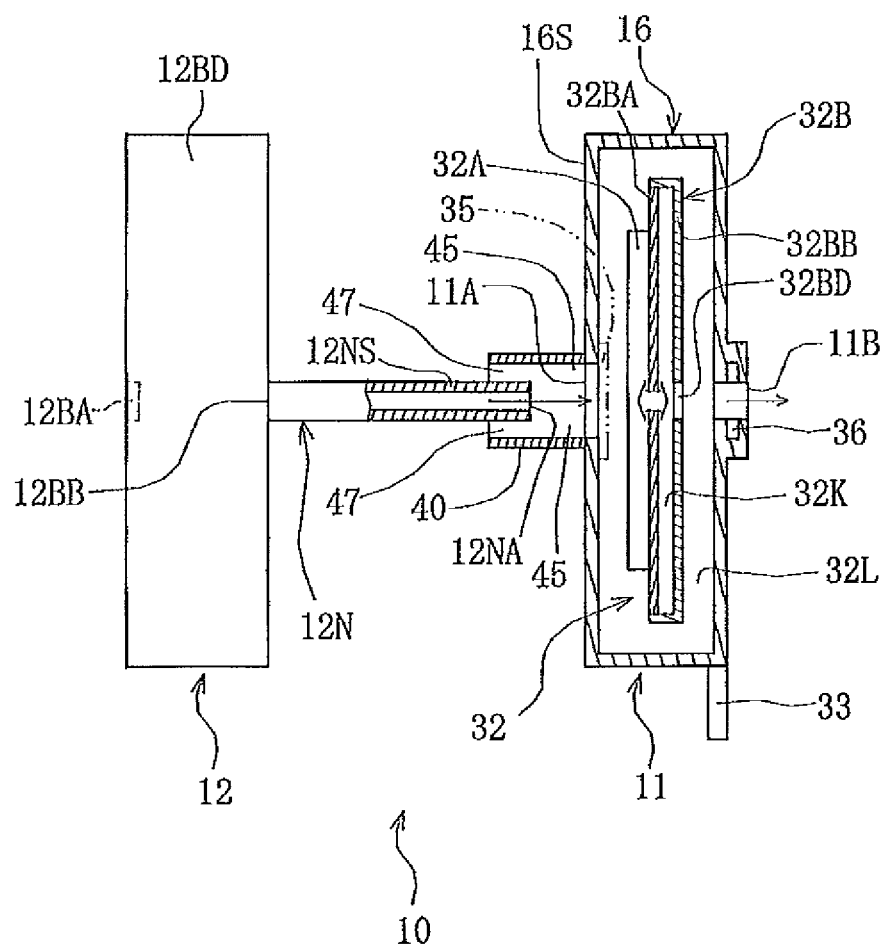
FIG. 6 is a partial cross-sectional view illustrating an outline of a second pump unit.

While the flow passage forming tube 40 is formed so as to expand from the micro pump 11 toward the assist mechanism 12 in the above-described embodiment, the flow passage forming tube 40 may be formed in a substantially uniform shape from the micro pump 11 toward the assist mechanism 12, i.e., in a linear shape (see FIG. 6).

Figure 7:
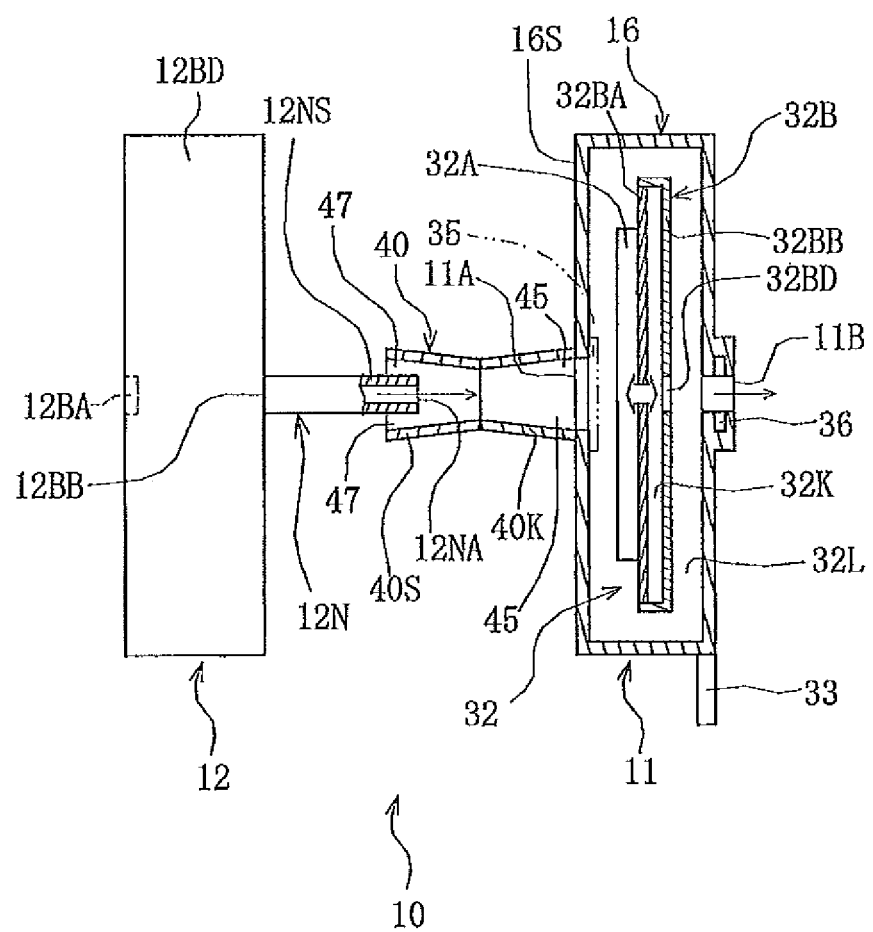
FIG. 7 is a partial cross-sectional view illustrating an outline of a third pump unit.
Figure 8:
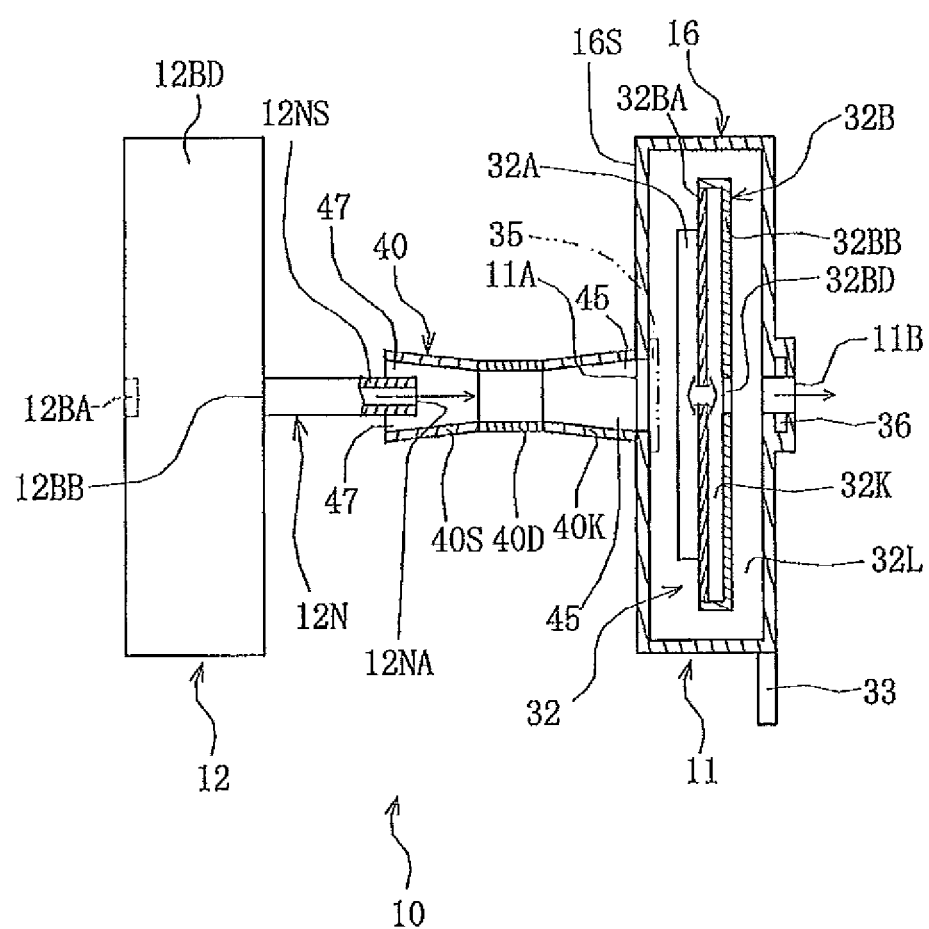
FIG. 8 is a partial cross-sectional view illustrating an outline of a fourth pump unit.

Alternatively, as shown in FIG. 7, the flow passage forming tube 40 may include: an expanding part 40K provided so as to project from the facing surface 16S of the housing 16 and expand from the assist mechanism 12 toward the micro pump 11; and a narrowing part 40S provided consecutively with an opening end of the expanding part 40K and expanding from the micro pump 11 toward the assist mechanism 12. Alternatively, a straight-flow part 40D, which is linear from the micro pump 11 to the assist mechanism 12, may be provided between the narrowing part 40S and the expanding part 40K (see FIG. 8). Furthermore, according to the flow passage forming tubes 40 shown in FIGS. 7 and 8, it is preferable that the position of the jet port 12NA be set in the narrowing part 40S. This allows the flow rate of a fluid at the inflow port 11A to be increased.

Figure 9:
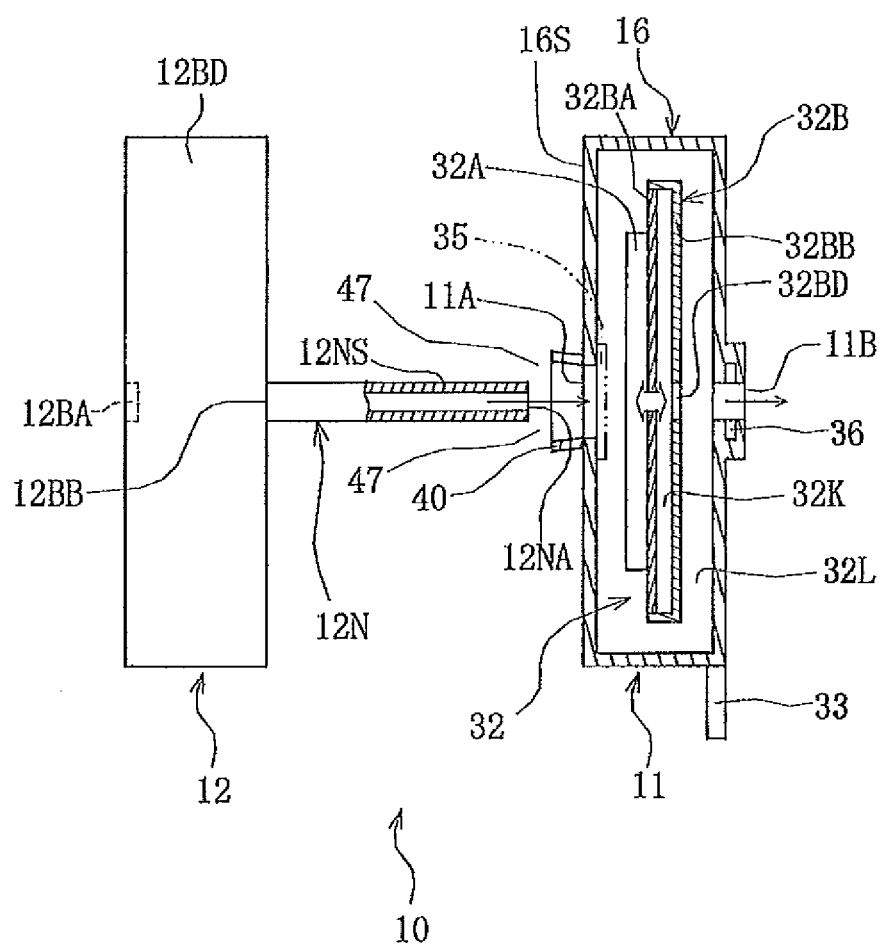
FIG. 9 is a partial cross-sectional view illustrating an outline of a fifth pump unit.

While the jet port 12NA is disposed inside the flow passage forming tube 40 in the above-described embodiment, the present invention is not limited thereto. As shown in FIG. 9, the jet port 12NA may be disposed outside the flow passage forming tube 40. An opening end of the flow passage forming tube 40 on the jet nozzle 12N side is located in proximity to the jet port 12NA. An opening size of the jet port 12NA is smaller than an opening of the flow passage forming tube 40 on the jet nozzle 12N side. A fluid present in the gap 47 formed by the jet nozzle 12N and the flow passage forming tube 40 flows toward the secondary blower chamber 32L by being pulled by a fluid jetted from the jet port 12NA and flowing toward the secondary blower chamber 32L. In this manner, the pump unit 10 can increase the flow rate of a fluid at the inflow port 11A as compared to a case where only the micro pump 11 is used for operation. Therefore, the pump unit 10 can increase the flow rate of a fluid at the outflow port 11B as compared to a case where only the micro pump 11 is used for operation.

Figure 10:
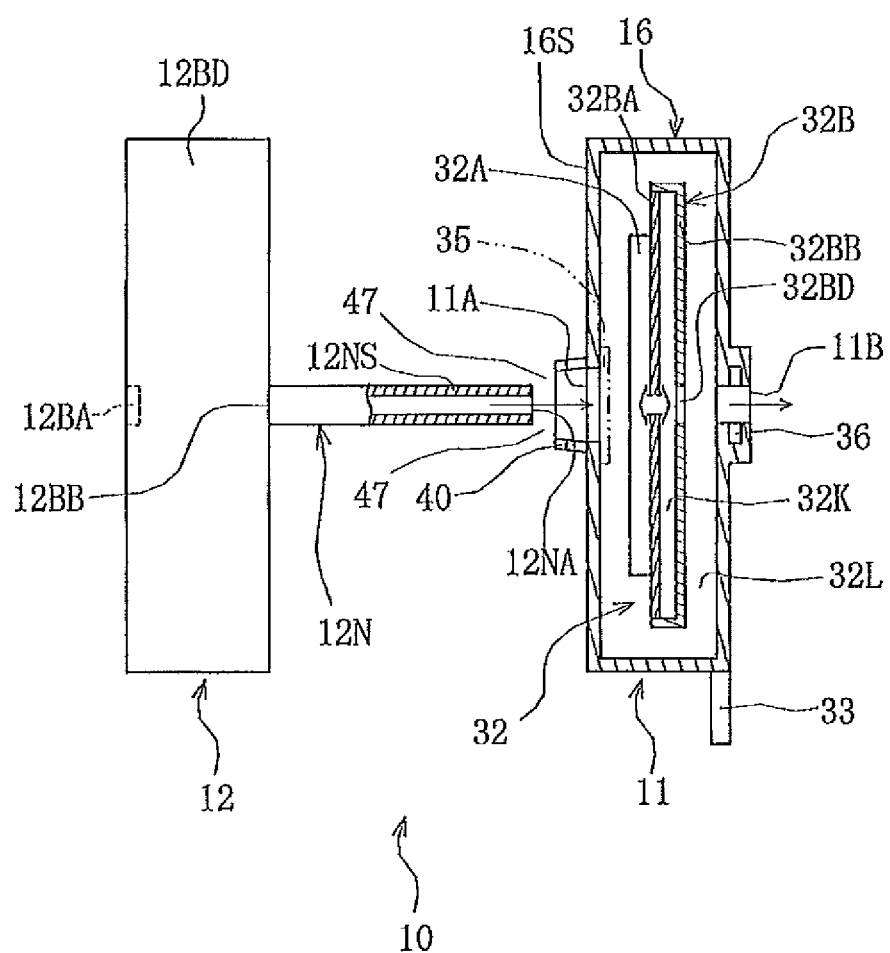
FIG. 10 is a partial cross-sectional view illustrating an outline of a sixth pump unit.

It is preferable that the jet port 12NA be directly facing the opening of the flow passage forming tube 40 on the jet nozzle 12N side. A shape of the flow passage forming tube 40 may be any one of a shape expanding from the micro pump 11 toward the assist mechanism 12 (see FIG. 9), a linear shape extending from the micro pump 11 to the assist mechanism 12, and a shape expanding from the assist mechanism 12 toward the micro pump 11 (see FIG. 10).

The flow passage forming tube 40 may be provided with a slit. The slit may be formed so as to extend in a flow direction of a fluid in the flow passage forming tube 40 (for example, the axial direction of the flow passage forming tube 40) or formed so as to extend in a direction intersecting with the flow direction of a fluid (for example, the circumferential direction). The slit extending in the flow direction of a fluid may be formed from one end of the flow passage forming tube 40 on the micro pump 11 side to the other end thereof, i.e., from one end (on the micro pump 11 side) to the other end (on the assist mechanism 12 side).

Figure 11:
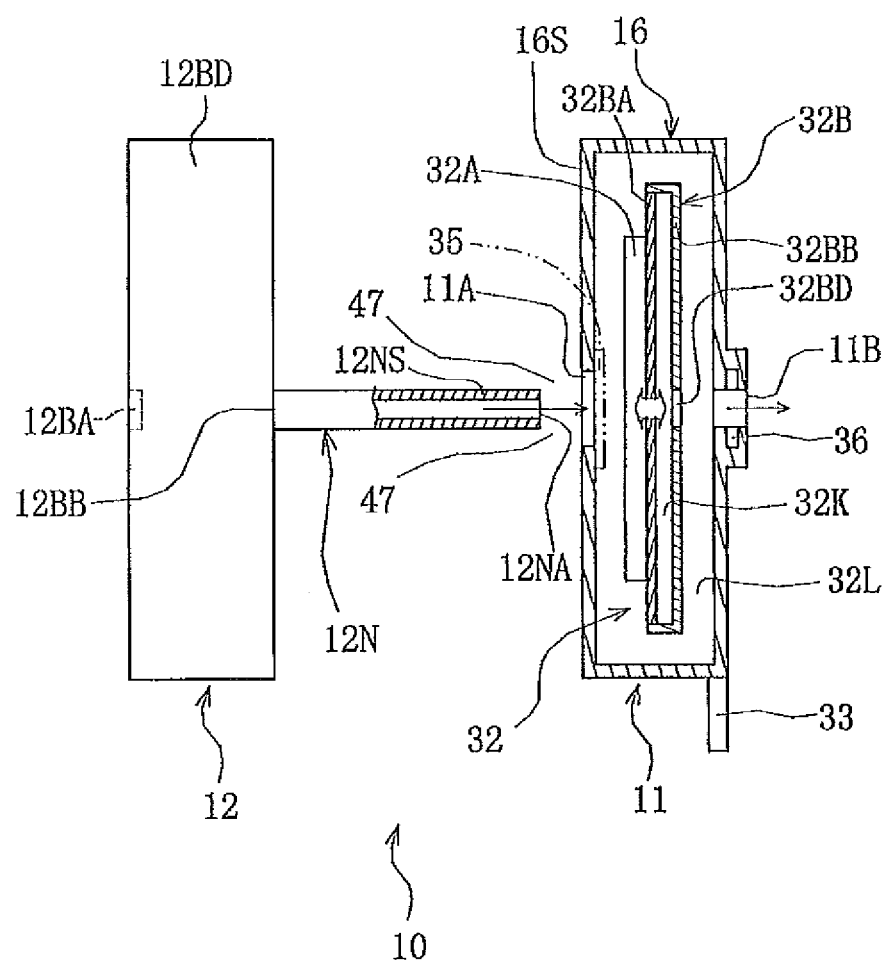
FIG. 11 is a partial cross-sectional view illustrating an outline of a seventh pump unit.

As shown in FIG. 11, the flow passage forming tube 40 may be omitted. In this case, the jet nozzle 12N is disposed in such a manner that the jet port 12NA is located in proximity to the inflow port 11A. An opening size of the jet port 12NA is smaller than that of the inflow port 11A. Also, it is preferable that the jet port 12NA be directly facing the inflow port 11A.

Figure 12:
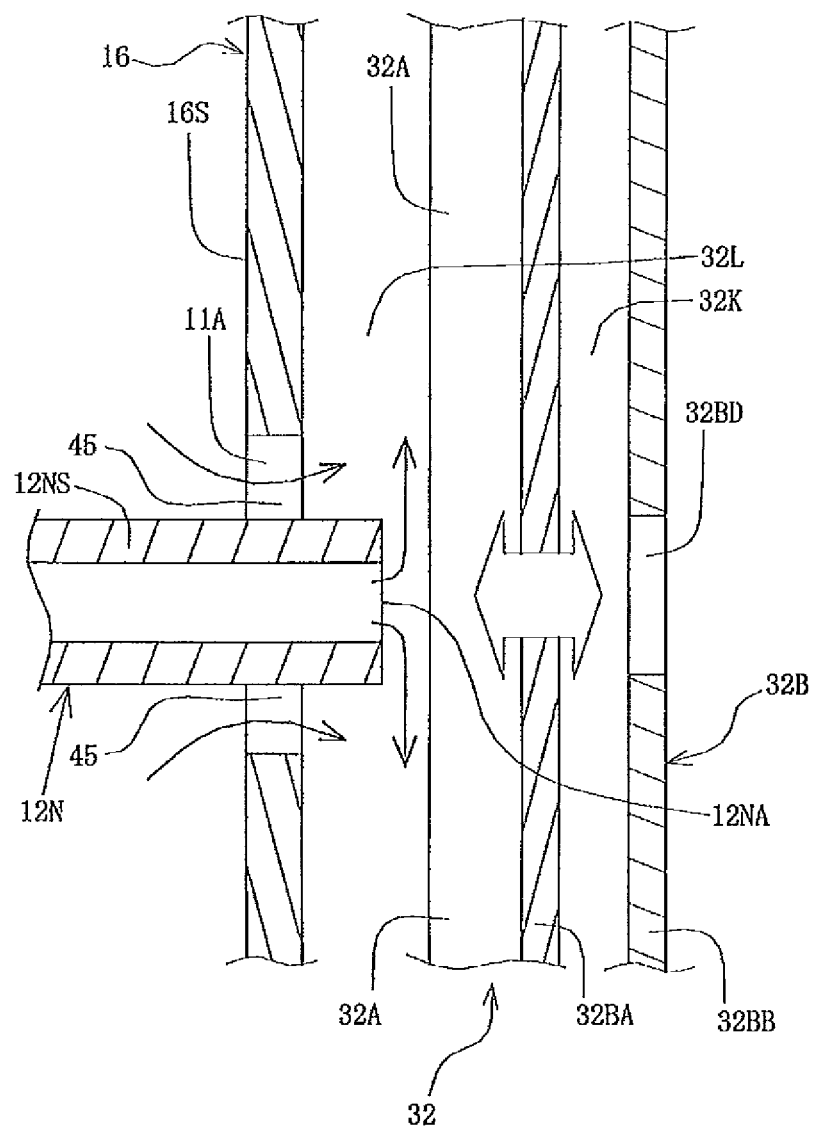
FIG. 12 is a cross-sectional view illustrating an outline of an eighth pump unit in the vicinity of an inlet portion of a micro pump.
Figure 13:
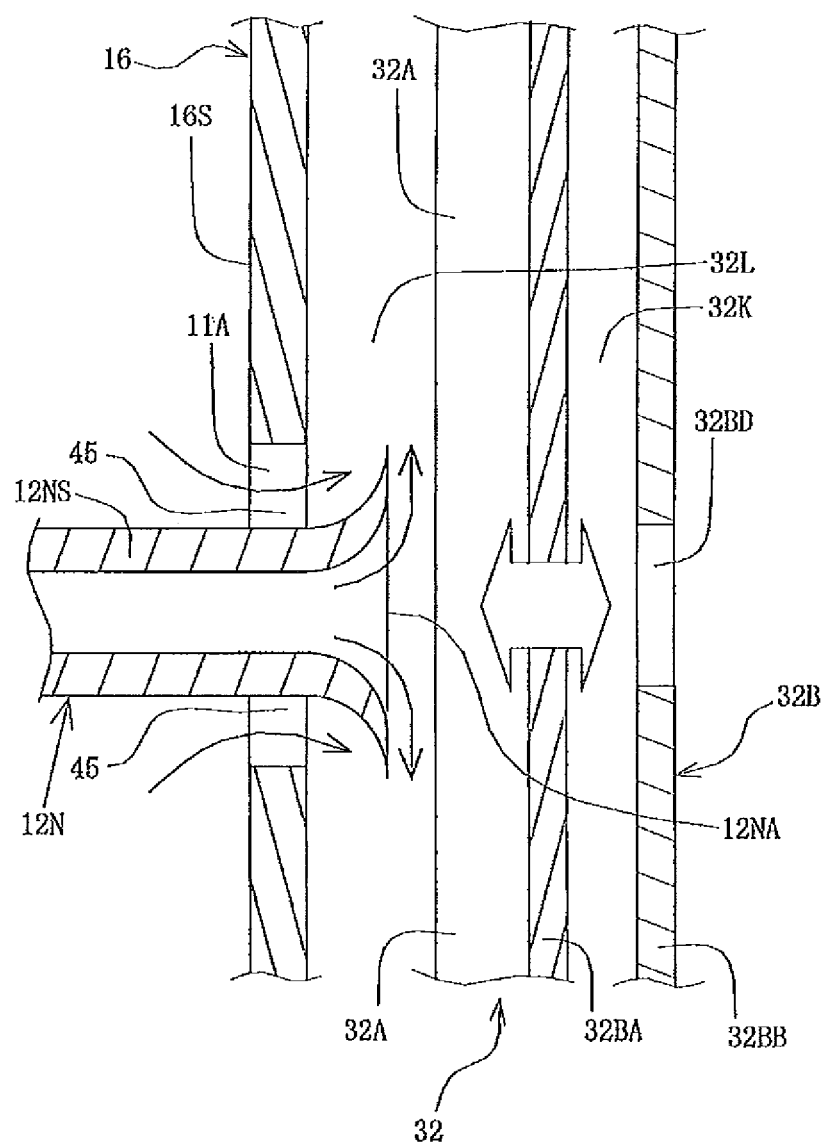
FIG. 13 is a cross-sectional view illustrating an outline of a ninth pump unit in the vicinity of an inlet portion of a micro pump.

Alternatively, the jet port 12NA may be positioned in the secondary blower chamber 32L as long as a fluid present in the gap 47 formed by the jet nozzle 12N and the peripheral portion of the inlet 11A is pulled toward the secondary blower chamber 32L by the fluid jetted from the jet port 12NA (see FIGS. 12 and 13). The tip portion 12NS of the jet nozzle 12N may have a uniform size from a base thereof to the jet port 12NA (see FIG. 12) or may be expanded from a base of the jet nozzle 12N toward the jet port 12NA (see FIG. 13). Note that the above-described flow passage forming tube 40 may be provided in the pump units 10 shown in FIGS. 12 and 13.

While the micro pump 11 is used as the pump body in the above-described embodiment, a pump unit including a plurality of micro pumps 11 may be employed. Similarly, a pump unit including a plurality of micro pumps 11 may be employed as the assist mechanism 12.

Another form of the assist mechanism 12 including a plurality of micro pumps 11 will be described next.

Figure 14:
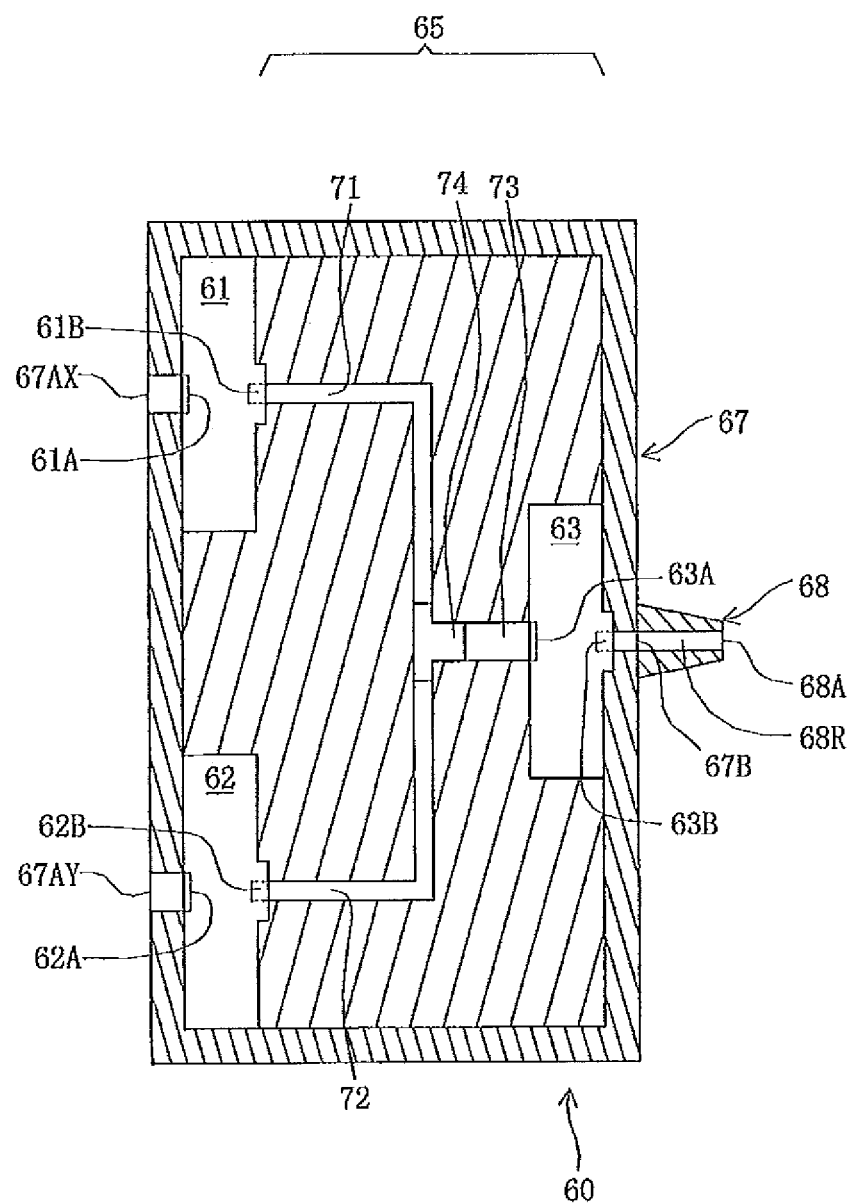
FIG. 14 is a cross-sectional view illustrating an outline of a second assist mechanism.

As shown in FIG. 14, an assist mechanism 60 includes a pump body and a jet nozzle 68 provided in the pump body. The pump body includes: micro pumps 61 to 63 each having a configuration similar to the micro pump 11; a confluent passage forming member 65 joining the micro pumps 61 to 63 together; and a housing 67 for housing the micro pumps 61 to 63 and the confluent passage forming member 65. The housing 67 is provided with inlets 67AX and 67AY through which a fluid outside the housing 67 enters the inside thereof; and an outlet 67B through which the fluid inside the housing 67 exits to the outside thereof. The inlet 67AX is directly connected to an inflow port 61A of the micro pump 61. The inlet 67AY is directly connected to an inflow port 62A of the micro pump 62. The outlet 67B directly connects to an outflow port 63B of the micro pump 63. The confluent passage forming member 65 includes: a flow passage 71 with one end directly connected to an outflow port 61B of the micro pump 61; a flow passage 72 with one end directly connected to an outflow port 62B of the micro pump 62; a flow passage 73 with one end directly connected to an inflow port 63A of the micro pump 63; and a confluent passage 74 to which the other ends of the respective flow passages 71 to 73 are directly connected.

The jet nozzle 68 is provided in the vicinity of the outlet 67B of the housing 67. The jet nozzle 68 includes a jet port 68A provided at a tip portion thereof and a flow passage 68R interconnecting the outlet 67B and the jet port 68A.

Operations of the assist mechanism 60 will be described next. The micro pumps 61 and 62 take a fluid in from the individual inlets 67AX and 67AY and discharge the fluid with an increased pressure from the outflow ports 61B and 62B as it is, respectively. Thus, as compared to a case where a fluid is taken in from one inlet provided in the housing 67 by means of a single micro pump, a fluid with a larger flow rate can be taken in and the pressure of the fluid can be increased to a pressure equivalent to that in such a case. The confluent passage forming member 65 allows the fluids whose pressure has been increased by the micro pumps 61 and 62 to merge. The merged fluid flows into the inflow port 63A of the micro pump 63 as it is. Here, the fluid when exiting from each of the micro pumps 61 and 62 has a volume smaller than that when being taken in from the individual inlet 67 due to its increased pressure. Thus, the flow rate of the fluid flowing into the inflow port 63A of the micro pump 63 through the confluent passage forming member 65 is large as compared to a case where a fluid is taken into the micro pump 63 directly from an inlet provided in the housing 67. The pressure of the fluid flowed into the inflow port 63A of the micro pump 63 is further increased by the micro pump 63. In this manner, the assist mechanism 60 can jet a fluid with a larger flow rate at a higher pressure. By sending a fluid into the inflow port 11A of the micro pump 11 as shown in FIG. 1, etc., by means of the assist mechanism 60, the static pressure P and the flow rate Q of a fluid at the outflow port 11B can be increased as compared to a case where only the micro pump 11 is used for operation.

Note that the number of the inlets 67AX and 67AY formed in the housing 67 is not limited to two. Three or more inlets may be formed. Then, the inlet formed in the housing 67 may be directly connected to an inflow port of a micro pump housed in the housing 67.

Figure 15:
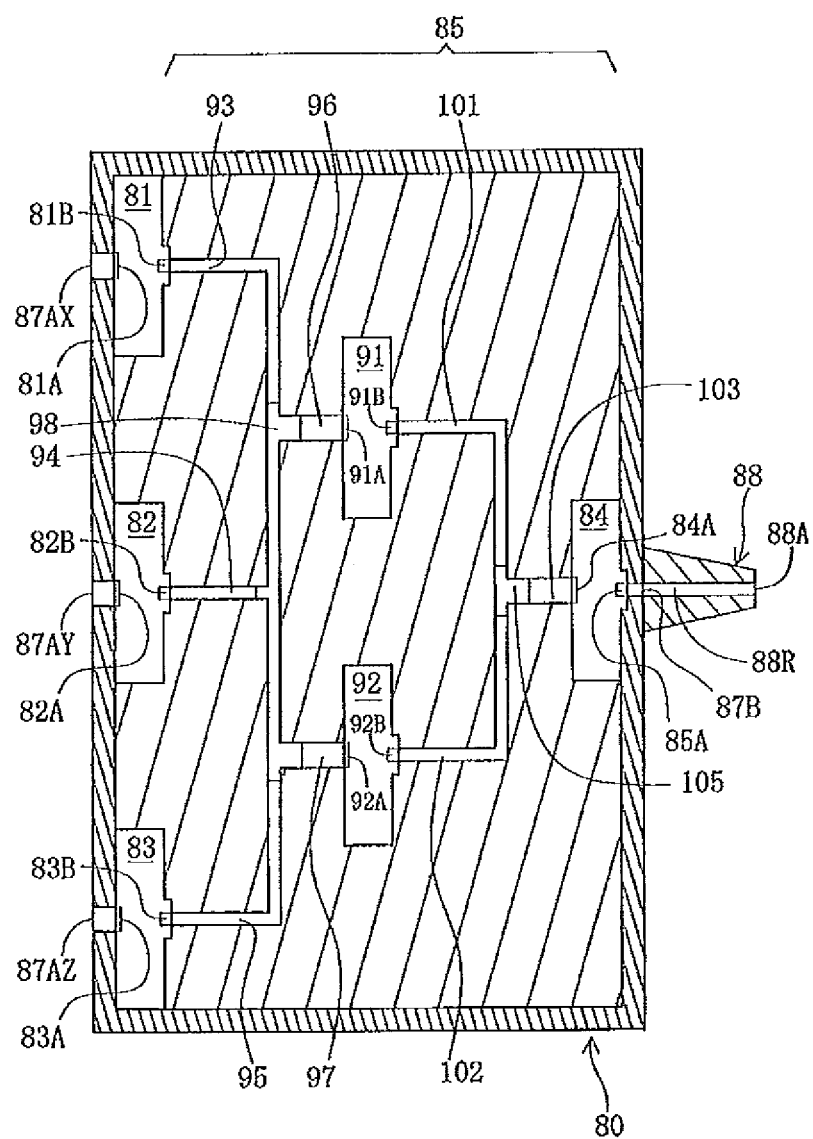
FIG. 15 is a cross-sectional view illustrating an outline of a third assist mechanism.

Alternatively, a micro pump may be provided between the micro pumps 61 and 62 and the micro pump 63. For example, as shown in FIG. 15, an assist mechanism 80 includes a pump body and a jet nozzle 88. The pump body includes: micro pumps 81 to 84 each having a configuration similar to the micro pump 11; a confluent passage forming member 85 joining the micro pumps 81 to 84 together; and a housing 87 for housing the micro pumps 81 to 84 and the confluent passage forming member 85. The housing 87 is provided with inlets 87AX, 87AY, and 87AZ through which a fluid outside the housing 87 enters the inside thereof; and an outlet 87B through which the fluid inside the housing 87 exits to the outside thereof. The inlet 87AX is directly connected to an inflow port 81A of the micro pump 81. Similarly, the inlet 87AY is directly connected to an inflow port 82A of the micro pump 82 and the inlet 87AZ is directly connected to an inflow port 83A of the micro pump 83. The outlet 87B is directly connected to an outflow port 85A of the micro pump 84. The jet nozzle 88 is provided in the vicinity of the outlet 87B of the housing 87. The jet nozzle 88 includes a jet port 88A provided at a tip portion thereof and a flow passage 88R interconnecting the outlet 87B and the jet port 88A.

The confluent passage forming member 85 includes: micro pumps 91 and 92 disposed between the micro pumps 81 to 83 and the micro pump 84; a flow passage 93 with one end directly connected to an outflow port 81B of the micro pump 81; a flow passage 94 with one end directly connected to an outflow port 82B of the micro pump 82; a flow passage 95 with one end directly connected to an outflow port 83B of the micro pump 83; a flow passage 96 with one end directly connected to an inflow port 91A of the micro pump 91; a flow passage 97 with one end directly connected to an inflow port 92A of the micro pump 92; a first confluent passage 98 to which the other ends of the respective flow passages 93 to 97 are directly connected; a flow passage 101 with one end directly connected to an outflow port 91B of the micro pump 91; a flow passage 102 with one end directly connected to an outflow port 92B of the micro pump 92; a flow passage 103 with one end directly connected to an inflow port 84A of the micro pump 84; and a second confluent passage 105 to which the other ends of the respective flow passages 101 to 103 are directly connected.

By sending a fluid into the inflow port 11A of the micro pump 11 as shown in FIG. 1, etc., by means of the assist mechanism 80, the static pressure P and the flow rate Q of a fluid at the outflow port 11B can be increased as compared to a case where only the micro pump 11 is used for operation.

The assist mechanism 12 composed of a plurality of micro pumps 11 may include the micro pumps 11 arranged in a lattice form, for example. Inflow ports and outflow ports of the micro pumps 11 arranged in a lattice form, an inlet formed in a housing, and an outlet formed in the housing are connected by a flow passage forming mechanism. The flow passage forming mechanism can transition between a parallel state in which a fluid introduced from the inlet is branched off and flowed into the micro pumps 11 arranged in a row direction and fluids exiting from the micro pumps 11 arranged in the row direction are merged and a serial state in which a fluid introduced from the inlet is serially flowed to the micro pumps 11 arranged in a column direction. When the flow passage forming mechanism is in the parallel state, the pump unit is set in a state where the flow rate Q of a fluid exiting from the outlet 11B is increased in preference to the static pressure P (a flow rate preferential transporting state). When the flow passage forming mechanism is in the serial state, the pump unit is set in a state where the static pressure P of a fluid exiting from the outlet 11B is increased in preference to the flow rate Q (a pressure preferential transporting state). Switching the flow passage forming mechanism among the parallel state, the serial state, and a state in which the parallel state and the serial state coexist as described above makes it possible to discharge a fluid with a predetermined static pressure P and a predetermined flow rate Q.

Figure 16A:
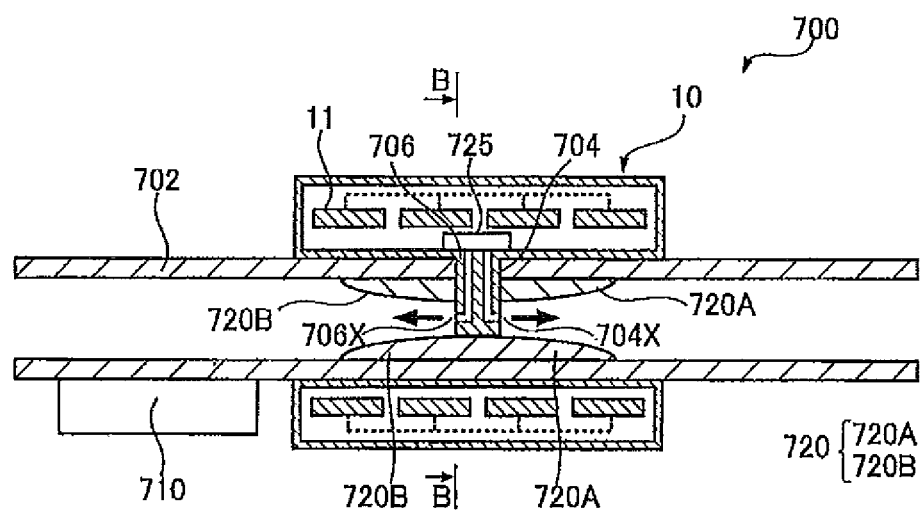
FIG. 16A is a cross-sectional view illustrating an outline of a respiratory assistance device.
Figure 16B:
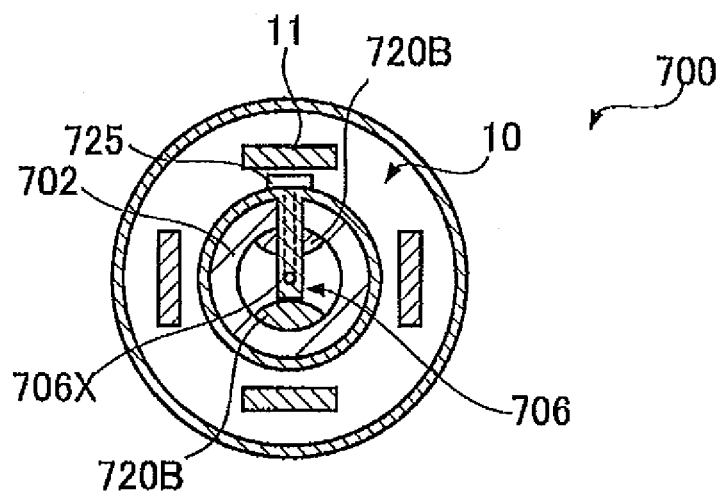
FIG. 16B is a cross-sectional view as viewed along arrows B-B in FIG. 16A.

FIGS. 16A and 16B illustrate an example in which the pump unit 10 is applied to a respiratory assistance device 700 for medical use. The respiratory assistance device 700 includes: a flow passage 702 through which an air for respiration (i.e., an expiratory air or inspiratory air) passes; an expiratory nozzle 704 and an inspiratory nozzle 706 disposed in the flow passage 702 and capable of releasing an acceleration air in an expiratory direction and in an inspiratory direction, respectively; the pump unit 10 disposed on an outer surface of the flow passage 702 in a circumferential direction thereof; and a battery 710 for driving the pump unit 10. The expiratory nozzle 704 is disposed closer to the expiratory direction side than the inspiratory nozzle 706 and can release an acceleration air from a release port 704X in the expiratory direction. The inspiratory nozzle 706 can release an acceleration air from a release port 706X in the inspiratory direction. The pump unit 10 supplies an acceleration air to each of the expiratory nozzle 704 and the inspiratory nozzle 706. Venturi walls 720 are disposed in the vicinity of the expiratory and inspiratory nozzles 704 and 706 disposed in the flow passage 702. The Venturi wall 720 includes: an inspiratory Venturi wall 720B extending from the inspiratory nozzle 706 in the inspiratory direction; and an expiratory Venturi wall 720A extending from the expiratory nozzle 704 in the expiratory direction. The thickness of the inspiratory Venturi wall 720B is gradually reduced in the inspiratory direction from the inspiratory nozzle 706. With such an inspiratory Venturi wall 720B, the acceleration air released from the inspiratory nozzle 706 spreads out (expands) as it moves in the inspiratory direction. As a result, a larger negative pressure is created in the inspiratory direction side than in the inspiratory nozzle side 706. Similarly, the thickness of the expiratory Venturi wall 720A is gradually reduced in the expiratory direction from the expiratory nozzle 704. Accordingly, the acceleration air released from the expiratory nozzle 704 spreads out (expands) as it moves in the expiratory direction. As a result, a larger negative pressure is created in the expiratory direction side than in the expiratory nozzle 704 side. It is also preferable that a plurality of inspiratory Venturi walls 720B be provided so as to interpose the release port 706X of the inspiratory nozzle 706. Similarly, it is preferable that a plurality of expiratory Venturi walls 720A be provided so as to interpose the release port 704X of the expiratory nozzle 704. Alternatively, the expiratory Venturi wall 720A and the inspiratory Venturi wall 720B may be formed integrally. Then, one expiratory Venturi wall 720A and one inspiratory Venturi wall 720B may together form one protruded body extending from the expiratory direction side toward the inspiratory direction side. Note that the battery 710 may be disposed at a remote location or may be omitted by connecting a power supply line.

Figure 17A:
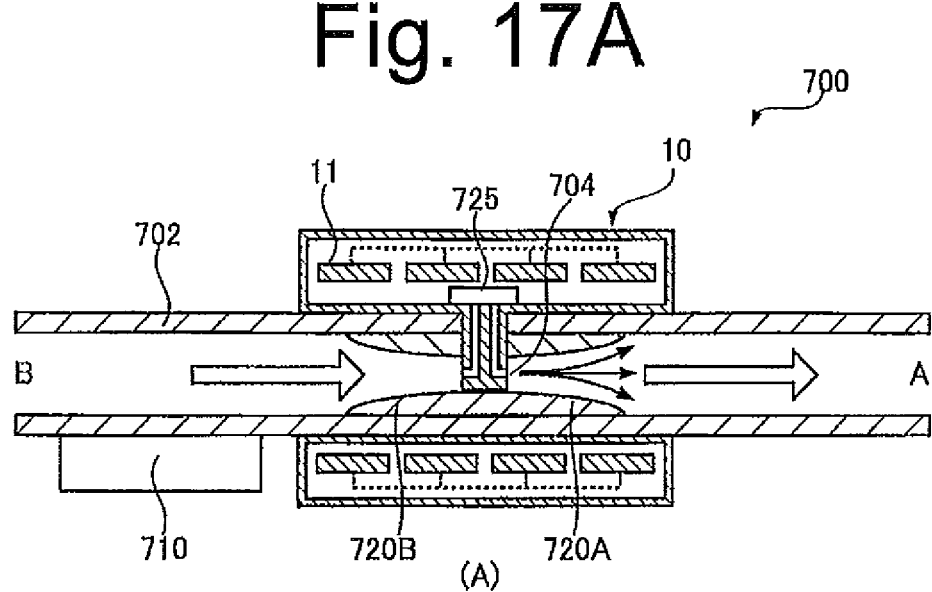
FIG. 17A is a cross-sectional view illustrating a control example of the respiratory assistance device.
Figure 17B:
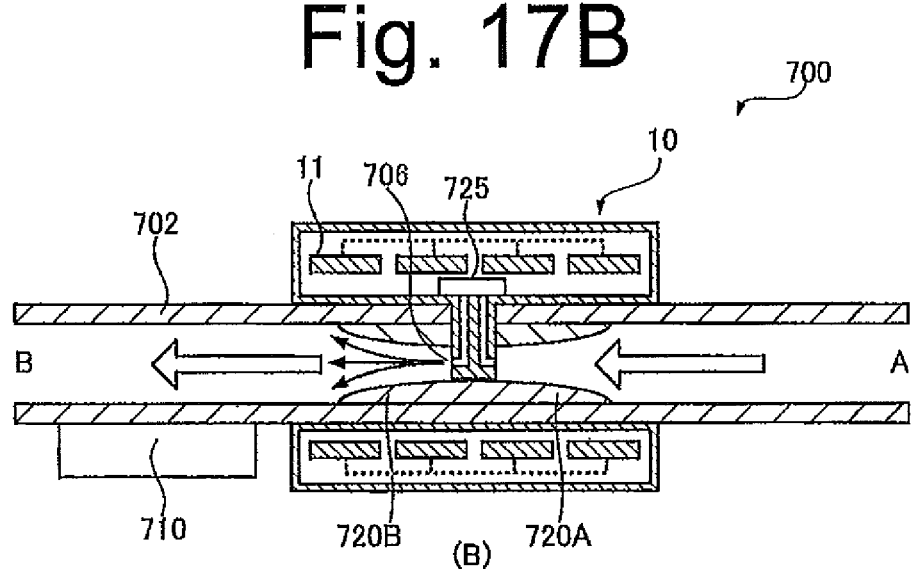
FIG. 17B is a cross-sectional view illustrating a control example of the respiratory assistance device.

Furthermore, an expiration and inspiration switching valve 725 (see FIG. 16A) is disposed in the vicinity of the outlet 87B of the pump unit 80 (see FIG. 15). The expiration and inspiration switching valve 725 switches between releasing an air to be discharged from the outlet 87B from the expiratory nozzle 704 provided in the jet nozzle 88 and releasing the air from the inspiratory nozzle 706 provided in the jet nozzle 88. When an air is released from the expiratory nozzle 704 as shown in FIG. 17A, this air is spread out by the expiratory Venturi wall 720A to set the expiratory side at a negative pressure. Thus, carbon dioxide discharged from the inspiratory side (lung side) B is drawn in to be flown toward the expiratory side A. Consequently, an expiratory action can be assisted. When an air is released from the inspiratory nozzle 706 as shown in FIG. 17B, on the other hand, this air is spread out by the inspiratory Venturi wall 720B to set the inspiratory side B at a negative pressure. Thus, oxygen supplied from the inspiratory side A is drawn in to be flown toward the inspiratory side (lung side) B. Consequently, an inspiratory action can be assisted.

According to the respiratory assistance device 700, the downsized pump unit 10 is directly fixed to a pipe itself that forms the flow passage 702. Thus, the respiratory assistance device 700 can be configured in an extremely compact manner. Furthermore, since the flow passage 702 and the pump unit 10 are formed integrally, the flow passage 702 and the pump unit 10 move together even when the flow passage 702 is moved along with a body movement of a user. Thus, the connection between the expiratory and inspiratory nozzles 704 and 706 and the pump unit 10 is prevented from being cut off. Therefore, stability in the respiratory assistance operation is increased and a user can move one's body more freely.

Furthermore, since a distance between the pump unit 10 and the expiratory and inspiratory nozzles 704 and 706 is reduced, responsiveness of the respiratory assistance operation can be enhanced.

Figure 18:
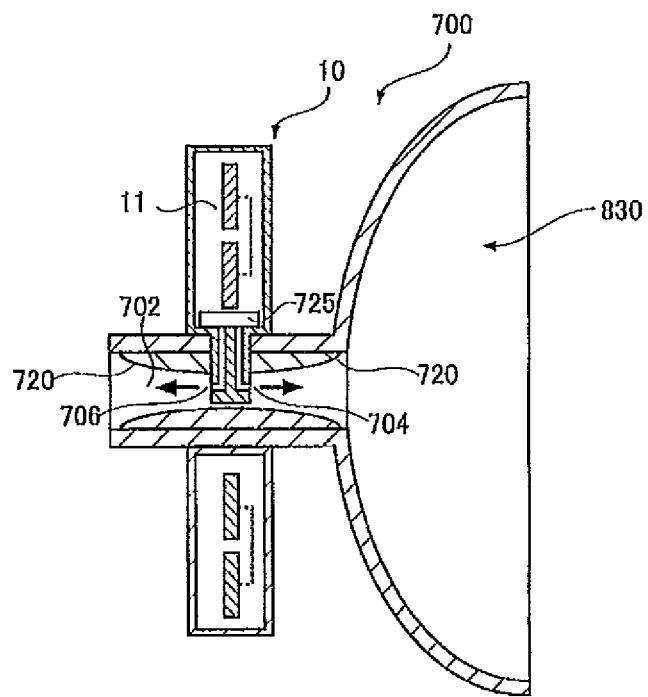
FIG. 18 is a cross-sectional view illustrating an outline of another respiratory assistance device.
Figure 19:
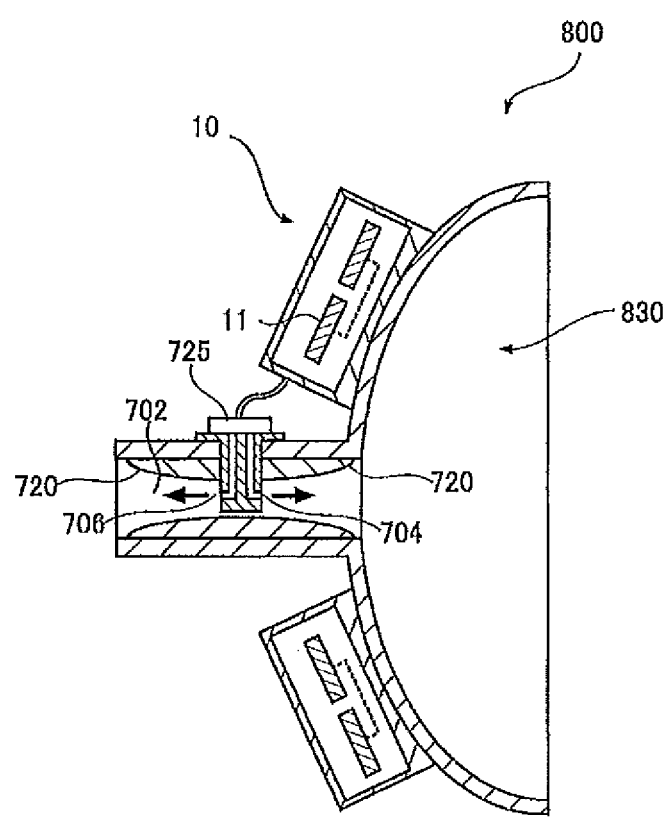
FIG. 19 is a cross-sectional view illustrating an outline of another respiratory assistance device.
Figure 20:
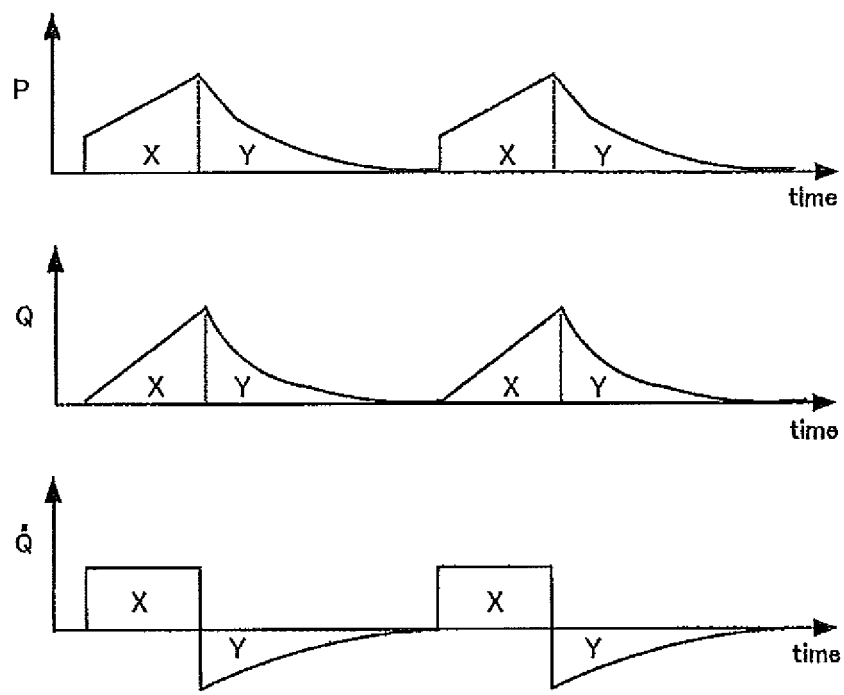
FIG. 20 shows graphs illustrating control examples of a pressure and a flow rate in a typical respiratory assistance device.

The respiratory assistance device 700 can be used in continuation with an intubation tube inserted into a windpipe through a mouth of a user. However, the respiratory assistance device 700 can also be used with the flow passage 702 being connected to a nose mask 830 as shown in FIG. 18, for example. Furthermore, when applied to a nose mask, it is preferable that the pump unit 10 be directly fixed to an outer peripheral surface of the nose mask 830 as in a respiratory assistance device 800 shown in FIG. 19, for example. Such an arrangement increases the overall stability. While the case where an air is supplied to the expiratory nozzle or the inspiratory nozzle by switching a single pump unit 10 with the expiration and inspiration switching valve 725 is illustrated here, two pump units 10 may be provided to connect to the expiratory nozzle and the inspiratory nozzle, respectively.

It is understood that the pump unit and the respiratory assistance device according to the present invention are not limited to the above-described embodiments and various modifications can be made thereto without departing from the scope of the present invention.

INDUSTRIAL APPLICABILITY

The pump unit according to the present invention can be used in various applications other than the respiratory assistance device. Also, the respiratory assistance device according to the present invention can be used for the respiratory assistance of various creatures.

The invention claimed is:

1. A pump unit comprising
a first pump body on an upstream side which sucks in a fluid outside a first housing into the housing through first inlet formed in a surface of the first housing and discharges the fluid to the outside of the first housing through a first outlet formed in the first housing by means of a first pump device housed in the first housing;
a second pump body on a downstream side which sucks in a fluid outside a second housing into the second housing through a second inlet formed in a surface of the second housing and discharges the fluid to the outside of the second housing through a second outlet formed in the second housing by means of a second pump device housed in the second housing; and
a jet nozzle provided at the first outlet of the first pump body on the upstream side, the jet nozzle including a jet port in a tip portion thereof and disposed at a position where a gap is formed by a peripheral portion of the second inlet of the second pump body on the downstream side and the tip portion.

2. The pump unit according to claim 1, wherein the jet port directly faces the second inlet.

3. The pump unit according to claim 1, comprising a tubular flow passage forming member projected from the surface of the second housing at the peripheral portion of the second inlet of the second pump body on the downstream side, the tubular flow passage forming member forming a flow passage of a fluid jetted from the jet port.

4. The pump unit according to claim 3, wherein the flow passage forming member has a narrowing part expanding in a direction from the second housing toward the jet nozzle.

5. The pump unit according to claim 3, wherein the flow passage forming member has an expanding part expanding in a direction from the jet nozzle toward the second housing.

6. The pump unit according to claim 3, wherein the jet port is positioned inside the flow passage forming member.

7. The pump unit according to claim 1, wherein the tip portion is passed through the second inlet.

8. The pump unit according to claim 1, wherein the jet nozzle expands toward the tip portion.

9. A respiratory assistance device comprising:
a flow passage through which an expiratory or inspiratory gas passes;
a nozzle disposed in the flow passage, the nozzle jetting an acceleration gas in an expiratory or inspiratory direction; and
the pump unit according to claim 1, the pump unit being fixed around the flow passage, the pump unit supplying the acceleration gas to the nozzle.

* * * * *